(12) United States Patent
Hofmann

(10) Patent No.: US 9,442,086 B2
(45) Date of Patent: Sep. 13, 2016

(54) METHOD AND APPARATUS FOR THE ANALYSIS OF WINE

(71) Applicant: Bruker BioSpin GmbH, Rheinstetten (DE)

(72) Inventor: Martin Hofmann, Bad Herrenalb (DE)

(73) Assignee: Bruker BioSpin GmbH, Rheinstetten (DE)

( * ) Notice: Subject to any disclaimer, the term of this patent is extended or adjusted under 35 U.S.C. 154(b) by 18 days.

(21) Appl. No.: 14/634,916

(22) Filed: Mar. 2, 2015

(65) Prior Publication Data

US 2015/0247814 A1 Sep. 3, 2015

(30) Foreign Application Priority Data

Mar. 3, 2014 (DE) .................. 10 2014 203 815

(51) Int. Cl.
| | |
|---|---|
| *G01N 24/08* | (2006.01) |
| *G01R 33/20* | (2006.01) |
| *G01N 33/14* | (2006.01) |
| *G01R 33/30* | (2006.01) |

(52) U.S. Cl.
CPC ............ *G01N 24/082* (2013.01); *G01N 24/08* (2013.01); *G01N 33/146* (2013.01); *G01R 33/30* (2013.01)

(58) Field of Classification Search
CPC ............. G01N 24/082; G01N 33/146; G01N 35/1079; G01N 24/08; G01R 33/30; B65B 31/027; B67D 1/0885; B67D 2001/0098; B67D 2001/0481
USPC .................. 324/300–322; 436/20; 73/864.01
See application file for complete search history.

(56) References Cited

U.S. PATENT DOCUMENTS

| | | | |
|---|---|---|---|
| 3,883,043 A | 5/1975 | Lane | |
| 4,550,082 A * | 10/1985 | Martin | ............... G01N 33/146 324/318 |
| 6,885,003 B1 | 4/2005 | Dubernet | |
| 7,712,385 B2 | 5/2010 | Bremer | |
| 2004/0090231 A1 | 5/2004 | Augustine | |
| 2005/0178801 A1 | 8/2005 | Lambrecht | |
| 2007/0137320 A1 | 6/2007 | Bremer | |
| 2010/0006603 A1 | 1/2010 | Weinberg | |
| 2011/0046896 A1* | 2/2011 | Smajlovic | ............ G01N 33/146 702/24 |

FOREIGN PATENT DOCUMENTS

| | | |
|---|---|---|
| DE | 2 001 311 | 7/1971 |
| DE | 195 37 124 | 4/1997 |
| EP | 1 798 551 | 6/2007 |
| WO | WO 2011/010616 | 1/2011 |

* cited by examiner

*Primary Examiner* — Melissa Koval
*Assistant Examiner* — Rishi Patel
(74) *Attorney, Agent, or Firm* — Paul Vincent

(57) ABSTRACT

A method for analyzing wine proposes puncturing the closure (60) of a wine bottle (61) containing wine (62) with a disposable cannula (3) having a lateral cannula opening (32) and a female Luer connection (30), and filling a disposable syringe (4) having a male Luer connection (41) with an inert gas. At least part (69) of the wine sample (65) is transferred into an analytical spectrometer (68) and spectrometric analysis of the wine sample (65) is carried out. An inexpensive method is thereby proposed that is easy to perform for analyzing a wine sample from a sealed wine bottle without impairing the quality or storage stability of the wine remaining in the wine bottle due to withdrawal of a wine sample from the wine bottle, in particular, wherein the volume of the removed wine sample can be easily controlled.

20 Claims, 10 Drawing Sheets

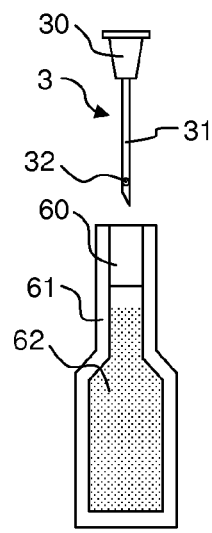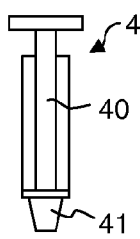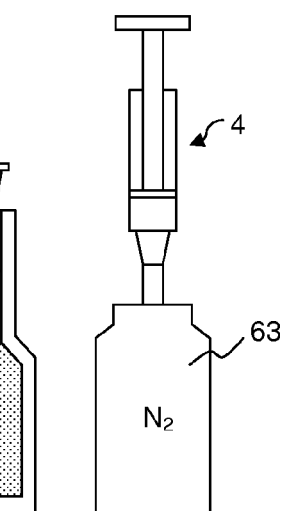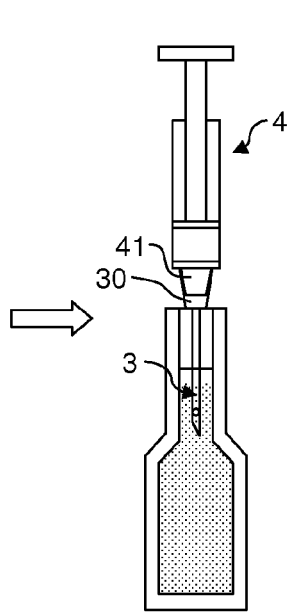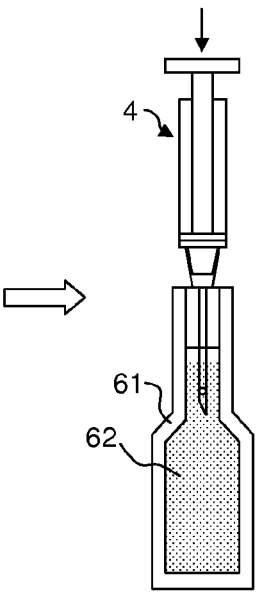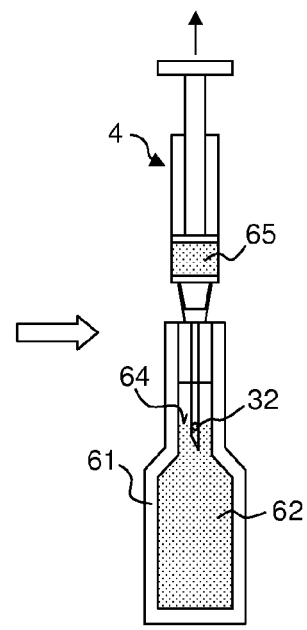
Fig. 1a    Fig. 1b    Fig. 1c    Fig. 1d    Fig. 1e

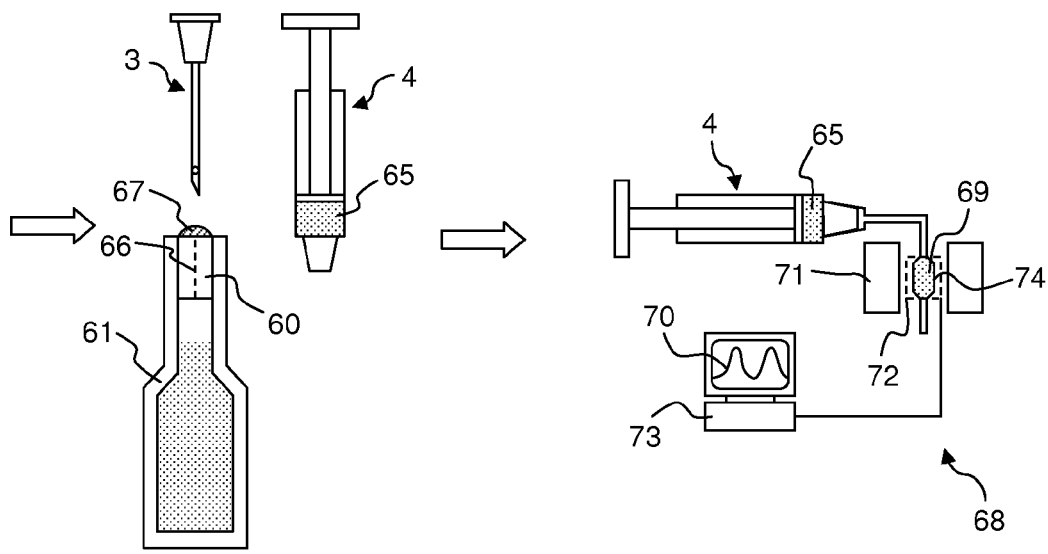
Fig. 1f       Fig. 1g
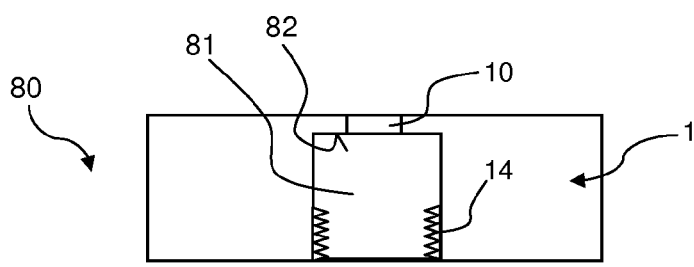
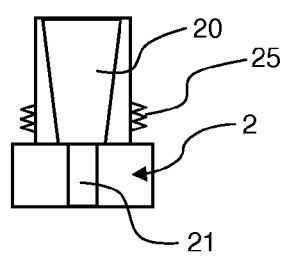
Fig. 2

METHOD AND APPARATUS FOR THE ANALYSIS OF WINE

BACKGROUND OF THE INVENTION

The invention concerns a method for analyzing wine, in which a wine sample is withdrawn from a wine bottle through the bottle closure, in particular, a closure made of cork oak or plastic material.

A method and a device for withdrawing wine from a sealed wine bottle without removing the cork from the wine bottle is disclosed in US 2005/0178801 A1.

The quality of a wine is determined by numerous factors, in particular, the combination of sugar, acid, phenols (including polyphenols), tannins and alcohol. It is the task of winemakers to harmonize this combination by trying to create qualitatively pleasant wines through selection of the grape varieties, the soil on which the vine is growing, the yeast used for the fermentation process and additionally the vinification process.

Wine changes when it comes into contact with atmospheric oxygen. For this reason, wine is substantially stored in gas-tight containers such as bottles or casks. Wine is usually exposed to ambient air only shortly prior to consumption.

Wine bottles were initially primarily sealed with cork from the bark of cork oaks. In the recent past, there has been a trend towards using corks made of plastic material. The cork is removed prior to drinking the wine and the wine contained in the bottle is usually poured out into drinking glasses. For this reason, the wine contained in the bottle comes into contact with a large amount of air. When the bottle is resealed, e.g. with a stopper, a considerable amount of air remains in the bottle above the wine. This contact with air is enough to impair the quality of the wine during further storage. For this reason, once a bottle has been opened, it is normally consumed within a relatively short time.

Prior art discloses some apparatus and methods of removing wine from a sealed bottle in order not to impair the quality or storage stability of the residual wine in the bottle.

The above-mentioned document US 2005/0178801 A1 proposes to pass a cannula through the cork, let some gas flow from a pressure gas cylinder through the cannula into the wine bottle by opening a valve, and after closing the valve, withdraw a corresponding amount of wine from the wine bottle through the cannula. Removal is performed by a removing device comprising the cannula, the pressure gas cylinder with pressure reducer, a valve means and a traversing mechanism for guiding the cannula relative to the wine bottle. The removing device is mechanically complex and the removed amount of wine is very difficult to control.

Further mechanisms for removing wine from sealed wine bottles are disclosed in US 2010/0006603 A1, WO 2011/010616 A1 and DE 24 49 861 A, which are each provided with double cannulas and also have a relatively complicated structure.

The quality of a wine is usually determined at competition tastings, and high-quality wines are given an award.

In addition to wine tastings, the quality of a specific wine can also be determined by means of chemical analysis. U.S. Pat. No. 6,885,003 B1, for example, discloses examination of the quality of grape must or wine by means of broadband infrared spectroscopy.

Only small volumes of a wine sample, in most cases only a few millimeters, are generally required for a spectroscopic analysis. In case of more expensive wines, it is generally not desired to sacrifice a whole wine bottle for withdrawing a wine sample for spectroscopy.

It is the underlying purpose of the invention to provide an inexpensive method which is easy to perform for analyzing a wine sample from a sealed wine bottle, wherein the removal of a wine sample does not considerably impair the quality or storage stability of the wine that remains in the wine bottle, in particular, wherein the volume of the withdrawn wine sample can be easily controlled.

SUMMARY OF THE INVENTION

This object is achieved in a surprisingly simple but effective fashion by a method for analyzing wine, comprising the following steps:

a) puncturing the closure of a wine bottle containing wine with a disposable cannula having a lateral cannula opening and a female Luer connection, and filling a disposable syringe having a male Luer connection with an inert gas, in particular nitrogen gas;

b) disposing the disposable syringe on the disposable cannula and pressing the inert gas contained in the disposable syringe into the wine bottle;

c) drawing up the disposable syringe while the cannula opening of the disposable cannula is immersed into the wine in the wine bottle such that the disposable syringe is filled with a sample of the wine;

d) removing the disposable cannula from the closure of the wine bottle;

e) transfer of at least part of the wine sample into an analytical spectrometer;

f) spectrometric analysis of at least that part of the wine sample.

Steps a) to d) of the inventive method, which concern the withdrawal of a wine sample from a sealed wine bottle, are well adapted to the requirements for spectroscopic examinations in accordance with steps e) and f). Readily available and inexpensive disposable items, i.e. a disposable cannula and a disposable syringe, are used within the scope of the inventive method for withdrawing the wine sample. Contamination of the wine sample or of the wine remaining in the wine bottle can be reliably prevented by using the disposable cannula and the disposable syringe only once. The gas and liquid volumes can moreover be easily manually controlled by means of a disposable syringe.

Puncturing the closure by means of the disposable cannula may be performed solely by the disposable cannula. For this purpose, an inventive device (see below) can be used as assistance. The disposable cannula can subsequently be easily connected to the disposable syringe via the Luer connections. Manual handling of the disposable syringe and the disposable cannula is therefore easy and safe. In particular, no auxiliary motor-driven means are required. The lateral opening of the disposable cannula is generally not clogged by the material of the closure (mostly cork oak bark).

Within the scope of the invention, inert gas (that does not react with the wine sample, e.g. $N_2$ or a noble gas such as argon) is initially pressed into the wine bottle in order to facilitate subsequent withdrawal of the sample and prevent drawing in of ambient air during or after the withdrawal of the wine. The volume of inert gas filled into the wine bottle can be exactly metered by means of the disposable syringe. In particular, the pressure in the wine bottle cannot increase in an undefined fashion.

The subsequently removed volume of the wine sample can then be exactly measured by means of the disposable syringe. Any waste of wine is prevented. The overpressure introduced into the wine bottle supports the withdrawal of the sample.

After removal of the disposable cannula, the puncture in the closure normally seals itself due to elastic expansion of the closure material towards the puncture.

After use, the disposable cannula and the disposable syringes can be quickly changed for withdrawing a sample from the next wine bottle. In particular, cleaning of components (e.g. the holder or the guiding component, see below) is not required in order to prevent cross contaminations since the disposable cannula and the disposable syringe are directly connected within the scope of the method.

Within the scope of the inventive proceeding, no or, if at all, a minimum amount of atmospheric oxygen is introduced into the wine bottle. The removed volume of the wine sample is replaced by inert gas such that any oxidation process is prevented. On the whole, the quality and the storage stability of the wine in the wine bottle remains practically unaffected.

After removal of the sample, the wine sample that has been taken can initially remain in the disposable syringe for further transport. Disposable syringes with check valve have proven to be useful in this case. The disposable syringe may also be sealed by a cap. The removed wine sample may also be transferred into another container.

The wine sample or a part thereof can then be moved in a fashion known per se into an analytical spectrometer and be measured with suitable measurement methods known per se in order to obtain an analytical spectrum of the measuring sample. If necessary, the wine sample may be prepared for the measurement prior to measurement e.g. by adjusting the ph value with suitable additives, setting of the temperature or addition of reference substances or carrier substances. The wine sample may also be subjected to separation methods (e.g. gas chromatography) and be spectroscopically examined in fractions.

The obtained analytical spectrum or the obtained analytical spectra give qualitative and quantitative information about the composition of the wine sample and therefore about the properties of the wine. Suitable reference measurements of a plurality of wine samples are preferably available by means of which, in particular, the grape variety, the geographical location (production area), the soil properties in the production area and/or the vintage of the wine can be identified or delimited. It is likewise easily possible to examine whether the content of a wine bottle corresponds to the label of the wine bottle in case a reference measurement of a wine sample in accordance with the label is available.

Within the scope of the present invention, the term wine includes all types of wine, in particular, wine produced from the grapes of a grape vine (including red wine, white wine, rosé wine, also liqueur/fortified wine such as port wine, sherry), and also fruit wine (in particular cherry wine, strawberry wine and apple wine (cider)), honey wine (mead) and rice wine. The alcohol content of an examined wine is typically between 8.5 vol % and 17.5 vol %, for liqueur/fortified wine also between 12 vol % and 22 vol %. The method is generally used for expensive (e.g. purchasing price of more than EUR 50 per bottle with 0.75 l) and/or old wines (e.g. older than 10 years) and prevents consumption of a whole bottle for withdrawing the wine sample. The closure (cork) to be punctured with the disposable cannula is typically made of cork oak or plastic material but may also contain e.g. parts of wax or sheet metal.

In one preferred variant of the inventive method, the volume of the inert gas filled in step a) into the disposable syringe is larger or equal to the volume of the wine sample filled in step c) into the disposable syringe. By drawing up (and filling into the wine bottle) an inert gas volume that is larger than the volume of the subsequently removed wine sample, a certain overpressure may remain in the wine bottle, which reduces the danger of ambient air diffusing into the wine bottle after removal of the wine sample. The additional volume is generally selected to be relatively small in order not to unnecessarily aggravate pressing the gas volume into the wine bottle. When the volumes of the inert gas and of the wine sample are equal, diffusion of air is at least not promoted by an underpressure during or after removal of the sample.

In another advantageous variant, the disposable cannula is rinsed with inert gas, in particular nitrogen gas, prior to puncture of the closure. This minimizes, in particular, entry of oxygen and carbon dioxide from the ambient air into the wine bottle. As far as possible, rinsing is performed just prior to puncture of the closure, e.g. 15 seconds or less prior to puncture of the closure.

In another advantageous variant, a puncture opening of the closure is sealed in an air-tight fashion in step d) after removing the disposable cannula, in particular, by a wax drop or a plastic cap. Sealing of the puncture opening reduces diffusion of atmospheric oxygen into the wine bottle after removal of the wine sample, if necessary, in addition to the sealing effect by the elastic closure of the puncture opening.

A disposable syringe with return valve is preferentially used as disposable syringe, in particular a monovette. The withdrawn wine sample is therefore automatically well protected against atmospheric oxygen after removal of the disposable cannula during further transport without requiring any further measures, such as e.g. a cap. In this case, the sample will not or only minimally change due to oxidation during further transport or provisional storage.

In one particularly preferred method variant, the spectrometric analysis is an NMR analysis. NMR (nuclear magnetic resonance) analysis provides particularly exact information about the wine sample. The inventive method largely excludes cross contaminations of the wine sample such that the high accuracy of the NMR analysis is particularly shown to advantage. In the NMR analysis within the scope of the invention, one-dimensional NMR spectra are typically determined via an FID (free induction decay) signal. Alternatively possible are also e.g. absorption spectrometric examinations in the infrared range, in the visible photo-optical and/or ultraviolet range.

The invention also concerns a device for performing steps a) to d) of an inventive method as described above, comprising:

A) a guide component,
comprising a guide channel for the disposable cannula,
comprising a receptacle for the female Luer connection of the disposable cannula,
and comprising a first coupling means for reversibly fastening the guide component to a holder component;

B) a holder component,
comprising a stop for a collar of the female Luer connection of the disposable cannula,
comprising a puncture opening providing access for the male Luer connection of the disposable cannula to the female Luer connection of the disposable cannula of a disposable cannula abutting the stop, and comprising a second coupling means that cooperates with the first coupling means for reversibly fastening the guide component to the holder component.

The inventive device enables insertion and alignment of a disposable cannula into/in the guide component and holding (clamping) thereof between the guide component and the holder component. The holder component is designed such that it can be gripped by one hand in order to thereby provide good control of the disposable cannula during manual puncture of the closure of the wine bottle by means of the disposable cannula. The stop in the holder component, on which abuts the collar formed at the end of the disposable cannula, enables transfer of force onto the disposable cannula in order to drive it through the closure or cork. The inert gas can subsequently be injected by the disposable syringe through the cannula and the wine sample can be withdrawn without having to remove the inventive device. For this purpose, the male Luer connection of the disposable syringe can be simply inserted through the puncture opening into the female Luer connection of the held disposable cannula. The device does therefore not get into contact with the wine sample such that any soiling of the device is basically irrelevant for the purity of the withdrawn wine sample. After removal of the sample, the disposable cannula can be easily exchanged by releasing the first and the second coupling device. The coupling devices are typically braced against each other by a rotary motion in order to clamp the disposable cannula between the guide component and the holder component.

In one particularly preferred embodiment of the inventive device, the first coupling means has an outer thread and the second coupling means has an inner thread. Mutual screwing of the guide component and the holder component by means of a thread is simple to realize and easy to manually operate and can, in particular, be easily used to press the disposable cannula against the stop of the holder component or brace the two components against each other. A bayonet mounting or snap-on mounting could alternatively also be used.

In one embodiment, the receptacle of the guide component is advantageously an anti-twist protection for the disposable cannula, in particular, wherein the receptacle of the guide component has two longitudinal slots or longitudinal grooves for engagement of two vanes formed on the female Luer connection of the disposable cannula. The anti-twist protection fundamentally facilitates puncture of the closure in practice, since the operator can enhance the advance motion of the disposable cannula in the closure by a rotary motion of the holder component, which rotary motion is then also carried out by the disposable cannula.

In one preferred embodiment, the guide component furthermore has a bell-like sleeve for receiving the bottle neck of the wine bottle. The device can be guided or centered along the bottle neck by means of the bell-like sleeve. The disposable cannula, which is arranged in the sleeve, is equally protected or the danger of unintended contact with the disposable cannula is reduced (in particular the danger of injury to the user).

In one advantageous further development of the above-mentioned embodiment, the bell-like sleeve projects past the tip of a disposable cannula accommodated in the guide component. The device can then be deposited on the guide component or its sleeve without damaging the tip of the disposable cannula (or the deposit area). The danger of injury to a user is additionally reduced and soiling of the needle tip is prevented.

In another advantageous further development of the above embodiment, the bell-like sleeve has one or more viewing windows. The viewing window enables easy control of the position of the disposable cannula, in particular, relative to the closure of the wine bottle.

In a further advantageous embodiment, the device moreover comprises: C) a cover component for covering the puncture opening of the holder component on a side facing away from the stop. This reduces the danger of injury to the user during puncture of the closure in case the needle of the disposable cannula should become detached from the female Luer connection of the disposable cannula and is pushed out to the rear through the puncture opening towards the hand of the user. The cover component then blocks the rear needle end. The cover component preferably has a thickness of at least 3 mm in the area that covers the puncture opening in case the cover component is produced of plastic material, and a thickness of at least 2 mm in case the cover component is produced of metal.

In one preferred further development of this embodiment, the cover component is designed as a stopper, in particular, wherein the stopper has a male Luer connection. A stopper is a simple and inexpensive measure to protect the user. The stopper can be inserted with the male Luer connection into the female Luer connection of a disposable cannula that is held in the device.

In another particularly preferred further development, the cover component is designed in the form of a lid that is rotatably or displaceably mounted on the holder component and has a recess that can be pivoted or displaced over the puncture opening. In one first position of the lid, in which the lid is preferably flush with the holder component to provide good manual access, the lid covers the puncture opening to protect the user. In a second, pivoted or shifted position of the lid, the recess allows access to the puncture opening or to the female Luer connection of the disposable cannula for the disposable syringe. The lid is preferably fastened to the holder component in an undetachable fashion.

In a particularly preferred embodiment of the inventive device, the holder component further comprises:
 a pressure gas connection for the inert gas,
 a female Luer connection,
 a manually switchable valve,
wherein the female Luer connection of the holder component is connected to the pressure gas connection via the switchable valve. In this embodiment, the holder component is simultaneously also used as inert gas filling aid for the disposable syringe. For filling the disposable syringe, the disposable syringe is inserted with its male Luer connection (spout) into the female Luer connection (gas port) of the holder component. Inert gas can then be filled into the disposable syringe by opening the valve. In case of suitable selection of the gas pressure, the disposable syringe can automatically slowly expand, if necessary, expansion (or drawing up) of the disposable syringe can also be manually supported. When the disposable syringe has been filled as desired, the valve can be closed again. The disposable syringe is then moved from the female Luer connection (gas port) in the holder component into the female Luer connection of the disposable cannula.

In another advantageous further development, the switchable valve is pretensioned into a closed position by the spring force of a spring. This facilitates handling. After termination of filling, the valve returns into the closed position by means of the spring force such that the filled disposable syringe can be immediately used again in accordance with the inventive method.

In one preferred further development, the female Luer connection of the holder component is disposed on the same side of the holder component as the side of the puncture opening facing away from the stop. For this reason, transfer of the disposable syringe from the Luer opening of the holder component to the Luer opening of the disposable cannula can be realized very quickly such that only little atmospheric oxygen can diffuse into the disposable syringe during transfer.

The present invention also concerns the use of a device in accordance with the invention as described above in a method in accordance with the invention as described above, wherein the disposable cannula is held between the guide component and the holder component during steps a), b), c) and d), and the disposable syringe is inserted through the puncture opening into the disposable cannula at least during steps b) and c). The wine sample can be comfortably manually withdrawn from the wine bottle with the aid of the device. If desired, the disposable syringe may also be inserted through the puncture opening into the disposable cannula during step d).

Further advantages of the invention can be extracted from the description and the drawing. The features mentioned above and below may be used in accordance with the invention either individually or collectively in arbitrary combination. The embodiments illustrated and described are not to be understood as exhaustive enumeration, rather have exemplary character for describing the invention.

The invention is illustrated in the drawing and is explained in more detail with reference to embodiments. In the drawings:

BRIEF DESCRIPTION OF THE DRAWING

FIGS. 1a-1g are schematic illustrations showing the process of a variant of the inventive method;

FIG. 2 shows a schematic cross-sectional view of a device for withdrawing a wine sample in accordance with the invention, comprising a guide component and a holder component in the disassembled state;

DESCRIPTION OF THE PREFERRED EMBODIMENT

Figure 3:
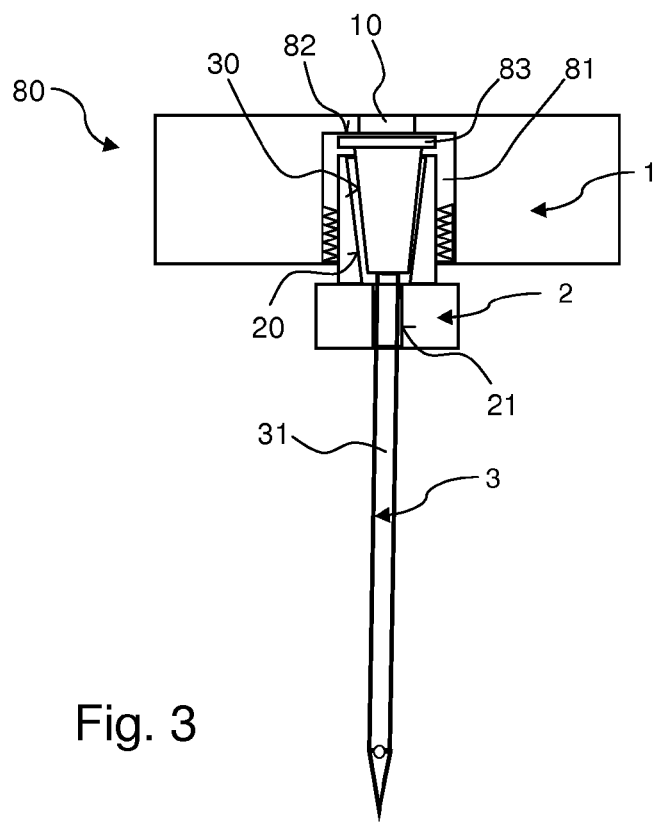
FIG. 3 shows a schematic cross-sectional view of the assembled device of FIG. 2 with inserted disposable cannula.

The so-called wine profiling provides a plurality of parameters that are relevant in view of quality and also safety within a few minutes on the basis of an NMR measurement of a wine sample. Conventional analysis (target analysis) is target-oriented towards certain known ingredients or properties of a wine. The NMR method can also provide target-oriented parameters but additionally also provide statistical evaluations within the same measurement such as classification and discrimination of wines based on statistical models of authentic samples. Thus, e.g. grape varieties can be verified or the geographical origin and vintage can be examined.

In view of the product quality, it is at first important to verify and check the information on the bottle label, and furthermore to check whether the concentration ranges of particular ingredients correspond to the specifications e.g. of the OIV (Organisation International Du Vin=International Wine Organization) or of governmental authorities. In case of Riesling, there is an international model that identifies the grape variety irrespective of whether it is German, Austrian, American or Australian Riesling. Germany and Austria have models that are established on the basis of authentic samples for identifying German and Austrian origin. If there are corresponding samples (references) it is possible to break the origin down to regionally limited areas. Vintages can also be differentiated from each other. There are currently models for the vintages 2011 and 2012. Systematic registration of authentic samples started in 2011. A statistical method is also important, which also reliably identifies unknown ingredients that were not specifically searched for. It is thus e.g. possible to detect contamination with detergents in as far as they show up in NMR. Admixture of larger portions of other grape varieties can also be detected.

The finger print detects all ingredients and portions thereof that show up through NMR. The NMR profiling is characterized by a unique reproducibility. This permits reliable detection of the concentration changes of many ingredients at the same time even when the changes are minimum. This permits e.g. detection of the geographical origin. Since NMR is a multimarker approach, the method reliably detects both simple and also sophisticated fakes. This is not possible with conventional methods that detect only a few or maybe even only one parameter. The detection of deviations from normality requires an accurate definition of what normality is. In the statistical sense, this means that a large number of authentic samples should be evaluated to describe the variability that normally occurs.

An NMR analysis of a wine sample requires only 1-2 ml per sample. In many cases and, in particular, in the case of expensive or old wines, one tries to avoid opening of an entire bottle to gain such a small sample amount. The contact with atmospheric oxygen is detrimental to long-term storage since the wine generates oxidation products under the influence of oxygen and therefore changes. When the bottles are closed, this process does not occur or is substantially slowed down. For this reason, a method of withdrawing a sample is required, which also functions without removing the cork/closure and minimizes or prevents contact with atmospheric oxygen.

The present invention is not limited to spectroscopic analysis by means of NMR but can also be used in connection with other spectroscopic methods in a corresponding fashion.

Wine Analysis Method in Accordance with the Invention

FIGS. 1a through 1g schematically illustrate the process of the inventive method for analyzing wine on the basis of one embodiment. The inventive wine withdrawal can be supported by a special device (cf. FIGS. 2-9d) which is not yet explained in FIGS. 1a-1g for reasons of simplicity.

As is illustrated in FIG. 1a, a wine sample shall be withdrawn from a wine bottle 61 that is sealed by a closure 60, e.g. a cork of cork oak or plastic material. The wine bottle 61 is filled with wine 62 (doted area). Contact between the wine 62 and atmospheric oxygen shall be prevented to a maximum degree during withdrawal of a wine sample in order not to impair the quality and the future storage stability of the wine 62.

For carrying out the inventive method, an unused disposable cannula 3 with female Luer connection (Luer adaptor) 30 and a single-channel hollow needle 31 with lateral cannula opening (side hole) 32 as well as an unused disposable syringe 4 with syringe plunger 40 and male Luer connection (Luer adaptor) 41 that matches the female Luer connection 30 are provided. If desired, the disposable cannula 3 may be rinsed with inert gas as a preparatory measure (not shown in detail).

In particular, a so-called "pencil-pointed-needle with side-hole", i.e. a pointed cannula with one or more lateral openings is suited as disposable cannula 3, wherein the outer diameter of the hollow needle is preferably at least 1.0 mm and maximally 2.5 mm and the length of the hollow needle is preferably at least 50 mm.

In a first step (step a) of the inventive method, cf. FIG. 1b, the closure 60 is punctured with the disposable cannula 3 and the disposable syringe 4 is filled with inert gas from an inert gas source 63, in the present case a nitrogen pressure gas container, by drawing up the disposable syringe 4, basically in arbitrary order. Drawing up may be performed manually or may also be supported by gas pressure from the inert gas source 63. It should be noted that, within the scope of the method, basically any inert gas source may be used and, in particular, no special pressurized cartridges are required. The disposable syringe 4 is preferably filled after puncture of the closure 60.

In a subsequent step, cf. FIG. 1c, the disposable syringe 4 that is filled with inert gas is then inserted with its male Luer connection (spout) 41 into the female Luer connection 30 of the disposable cannula 3. The inert gas contained in the disposable syringe 4 is then pressed into the wine bottle 61, cf. FIG. 1d. This can be easily manually performed provided that the inert gas volume is small in comparison with the gas volume above the wine 62 in the wine bottle 61. In conventional wine bottles 62, the gas volume above the wine 61 is normally approximately 10 ml or more such that an inert gas volume of 5 ml or less, preferably 2 ml or less, can be easily pressed into the wine bottle 61, generating a slight overpressure in the wine bottle 62. FIGS. 1c and 1d illustrate the step b) of the inventive method.

The disposable syringe 4 is subsequently (step c) of the inventive method) drawn up while the lateral cannula opening 32 is disposed below the surface 64 of the wine 62 cf. FIG. 1e. When the wine bottle 61 is filled to a sufficient level or the needle has a sufficient length, this can be realized as illustrated with the wine bottle 62 standing upright. Otherwise, the wine bottle 61 may also be tilted or turned upside down during drawing up of the disposable syringe 4. The overpressure 61 that prevails in the wine bottle 61 supports drawing up of the disposable syringe 4. A small part of the wine 62 of the wine bottle 61 is drawn up into the disposable syringe 4 and this drawn-up part is called wine sample 65. The volume of the wine sample 65 is typically 2 ml or less, preferably 1 ml or less.

The disposable cannula 3 may subsequently (step d) of the inventive method) be removed from the closure 60, cf. FIG. 1f, wherein the puncture opening 66 of the closure 60 generally automatically seals itself again due to the elastic properties of the closure material. The puncture opening 66 may alternatively or additionally be sealed by applying a wax drop 67 to the closure 66 at the location of the puncture opening 66. The disposable syringe 4 is typically removed from the disposable cannula 3 prior to removing the disposable cannula 3 from the closure 60. It is, however, also possible to remove the disposable cannula 3 together with the inserted disposable syringe 4 and remove the disposable syringe 4 from the disposable cannula 3 only after that. The removed used disposable cannula 3 is thrown away.

The wine sample 65 is then transported, e.g. inside the disposable syringe 4, to an analytical spectrometer 68. At least part 69 of the wine sample 65 is transferred into the analytical spectrometer 68 (in accordance with step e) of the inventive method), in the present case via a tubing in a flow rate measuring cell 74, cf. FIG. 1g.

In the present case, the analytical spectrometer 68 is an NMR spectrometer with magnet 71, RF resonator 72 and control and evaluation means 73. The specified part 69 of the wine sample 65 is then subjected to a spectrometric analysis in accordance with step f) of the inventive method. The obtained spectrum 70 gives information about the qualitative and quantitative composition of the wine sample 65.

The used disposable syringe 4 is thrown away at the latest after termination of the measurement of the wine sample 65 or of the part 69 thereof and is, in particular, not used again for withdrawing further wine samples.

Inventive Device for Withdrawing Wine

FIG. 2 shows an embodiment of an inventive device 80 for performing the method steps a) through d) of the above-described method for analyzing wine in a schematic cross-section in the disassembled state, i.e. prior to jamming (clamping) of a disposable cannula.

The device 80 comprises a holder component (needle holder) 1 and a guide component (needle guide) 2.

The guide component 2 has a straight guide channel 21 for the hollow needle of the disposable cannula and a substantially conical receptacle 20 for the female Luer connection of the disposable cannula. An outer thread is moreover provided on the outer side in the area of the receptacle 20 as a first coupling means 25.

In this case, the holder component 1 has a disc-like structure with a diameter that can be easily gripped around with one hand, typically approximately 6 cm to 10 cm. The holder component 1 has a recess (opening) 81 on its lower side for receiving an upper part of the guide component 2. The recess 81 can be accessed from the upper side of the holder component 1 via an opening 10, in the present case a central bore of the holder component 1. The opening 10 is narrowed compared with the recess 81 such that a stop 82 around the opening 10 can be used for the disposable cannula (not shown, cf. FIG. 3). The recess 81 moreover has an inner thread as a second coupling means 14, into which the outer thread of the guide component 2 can be screwed.

FIG. 3 shows the device 80 of FIG. 2 in the assembled state with a disposable cannula 3, the female Luer connection 30 of which is held (clamped) between the guide component 2 and the holder component 1. An upper collar 83 of the female Luer connection 30 abuts the stop 82 of the holder component 1. The female Luer connection 30 of the disposable cannula 3 moreover abuts the receptacle 20 of the guide component 2. The hollow needle 31 projects through the guide channel 21 of the guide component 2 with minimum play. The guide component 2 was screwed with its outer thread as far as possible into the inner thread of the recess 81. The recess 81 is substantially occupied by the upper part of the guide component 2 and by the female Luer connection 30 of the disposable cannula 3.

The upper opening of the female Luer connection 30 is located directly below the opening 10 of the holder component 1 and is therefore accessible through the opening 10.

Figure 4:
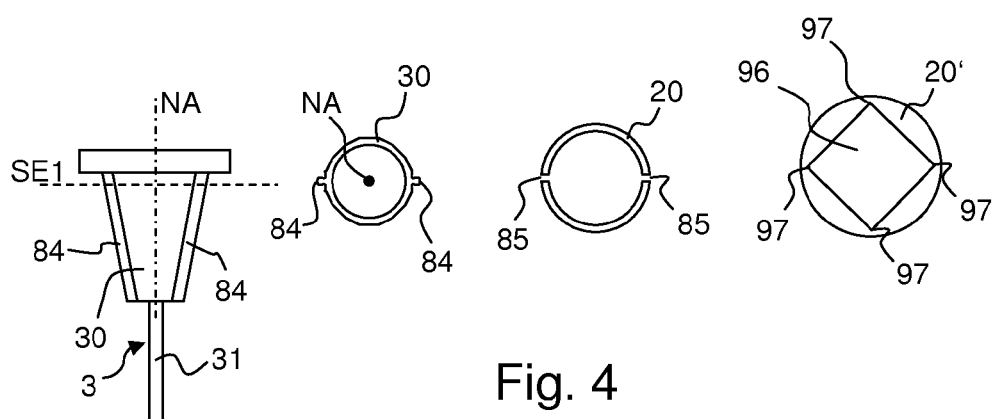
FIG. 4 shows schematic sectional views of the disposable cannula in the area of the female Luer connection and the receptacle of the guide component of FIG. 3, in each case perpendicular to the needle axis.

In the embodiment shown, the disposable cannula 3 is mounted in the receptacle 20 in a torsion-proof fashion as is illustrated in the cross-sections perpendicular to the direction of extension of the hollow needle 31 (in FIG. 3 from the top to the bottom), cf. FIG. 4. The left-hand side of FIG. 4 shows a side view of the disposable cannula 3 in the area of the female Luer connection 30 with the plane of intersection SE1 being drawn with dashed lines. The cross-section of the female Luer connection 30 of the disposable cannula 3 at this sectional plane SE1 is illustrated on the left-hand side of the middle figures. A cross-section of the receptacle 20 at the level of the sectional plane SE1 is illustrated on the right-hand side of the middle figures.

The female Luer connection 30 has two lateral, radially projecting vanes 84 in cross-section. These engage in longitudinal recesses 85 of the receptacle 20 in the clamped state of the disposable cannula 3. For this reason, the disposable cannula 3 can no longer rotate about the needle axis NA, in particular, when the disposable cannula 3 is driven into the closure of the wine bottle.

The receptacle 20' could alternatively also be designed to have a rectangular cross-section 96 as is illustrated in the cross-sectional view at the level of the intersecting plane SE1 on the right-hand side of FIG. 4, wherein the inner corners 97 prevent rotation of the laterally, radially projecting vanes 84.

Figure 5:
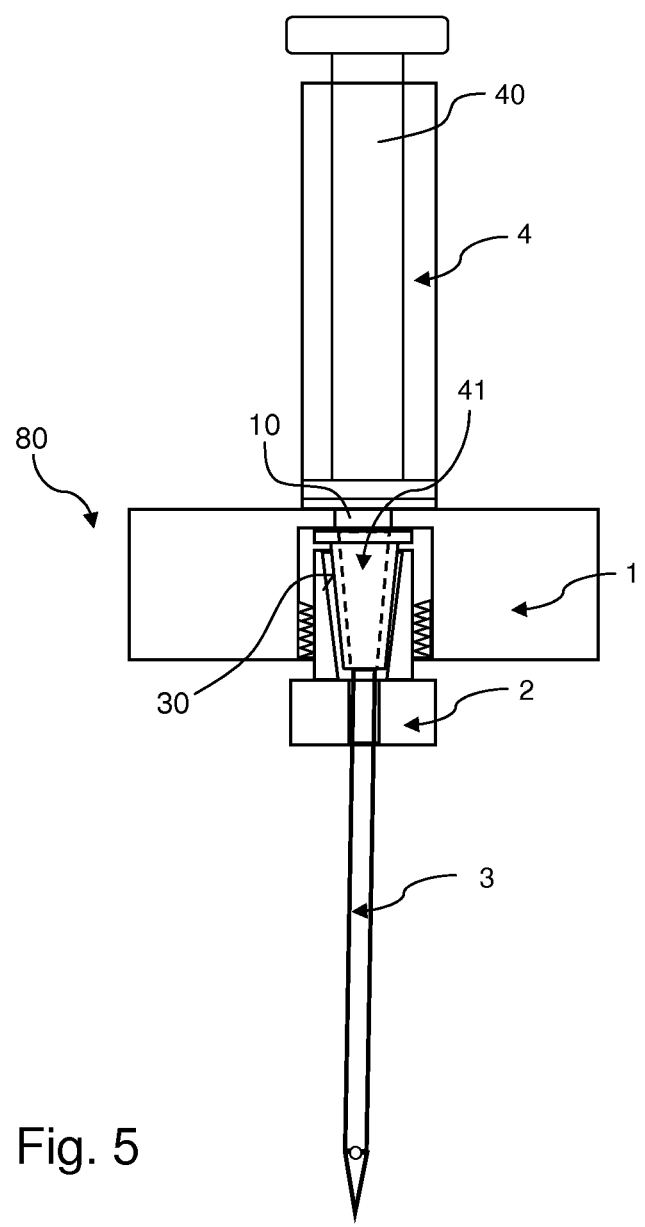
FIG. 5 shows a schematic cross-sectional view of the device of FIG. 3 with inserted disposable syringe.

FIG. 5 shows the device 80 of FIG. 3 with attached disposable syringe 4. The disposable syringe 4 has a male Luer connection 41 (dashed lines) which is inserted through the opening 10 into and coupled to the female Luer connection 30 of the disposable cannula 3. For this reason, inert gas can be transported from the disposable syringe 4 directly into the disposable cannula 3 or a wine sample can be transported from the disposable cannula 3 directly into the disposable syringe 4.

It should be noted that the disposable cannula 3 is typically held in an inventive device 80 during steps a), b), c) and d). The disposable syringe 4 is typically inserted through the opening 10 into the disposable cannula 3 only during steps b) and c) but can, however, also remain inserted in the disposable cannula during step d), if desired.

Figure 6A:
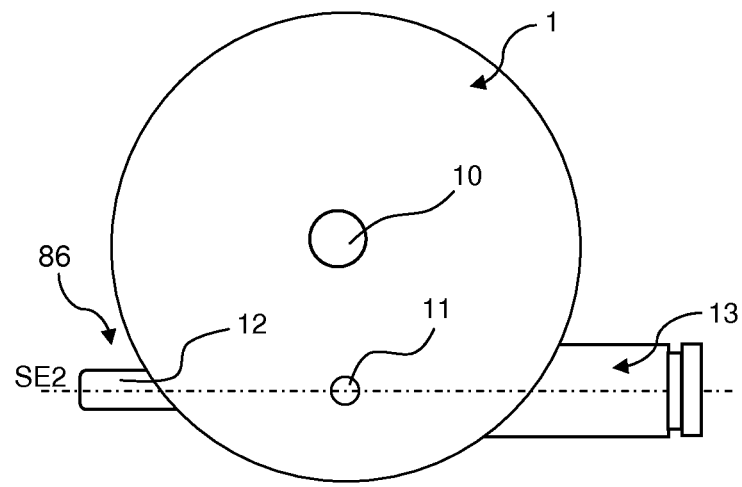
FIGS. 6a, 6b show a schematic top view (FIG. 6a) and a schematic cross-sectional view (FIG. 6b) in the area of the plane SE2 of FIG. 6a of a holder component in accordance with the invention with inert gas supply, with closed valve.
Figure 6B:
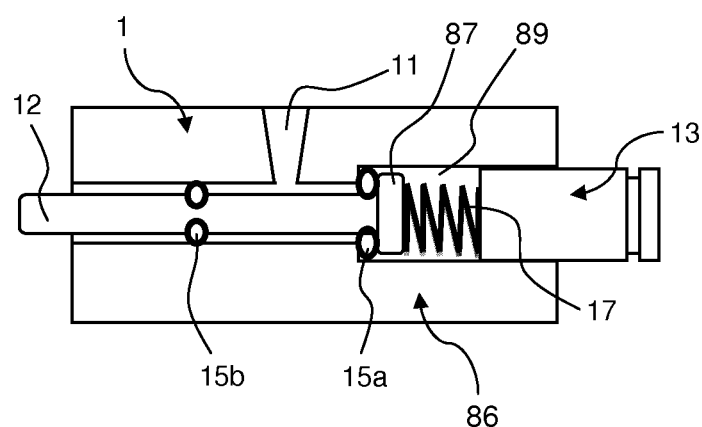
Figure 6C:
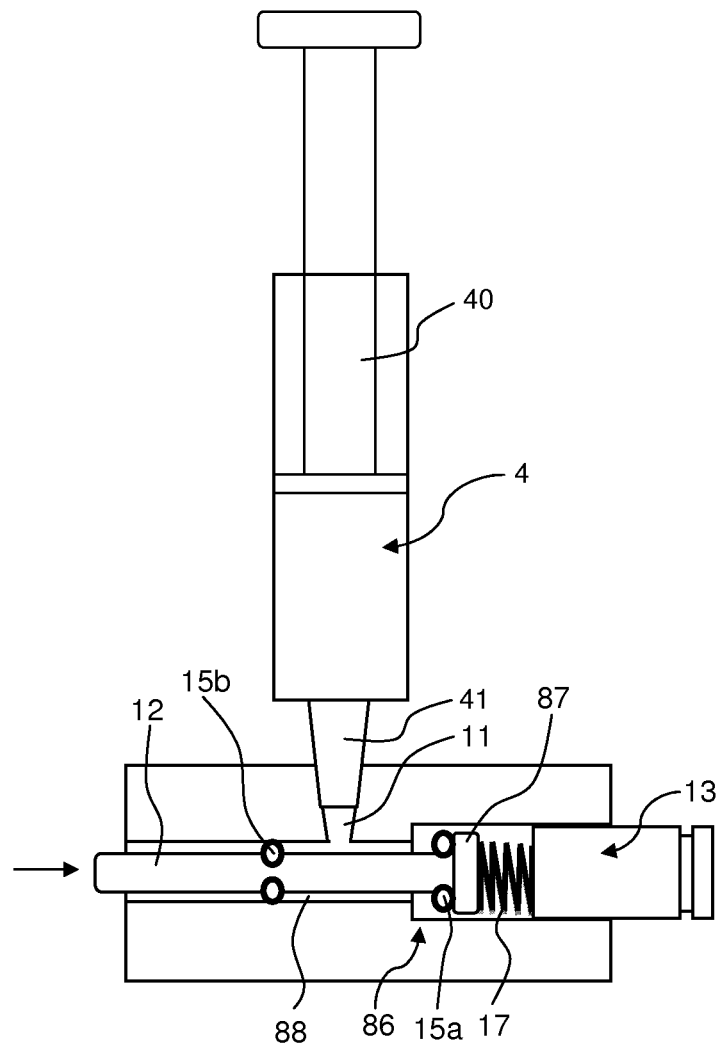
FIG. 6c shows the holder component of FIG. 6b with inserted disposable syringe and opened valve.

The inventive device 80 may be provided with an inert gas source as explained in FIGS. 6a through 6c in order to fill the disposable syringe 4 with inert gas during step a) of the inventive method.

FIG. 6a initially shows a top view of a holder component 1 similar to FIG. 2. In addition to the opening 10, the upper side of the holder component 1 is also provided with a female Luer connection 11 as a gas port. The holder component 1 moreover has a pressure gas connection 13 which is connected to a pressure gas reservoir with inert gas (preferably $N_2$ or also noble gas such as argon) by means of normal lines (e.g. fabric tubes) in a manner not shown in detail. A compression die 12 of a switchable valve 86 is moreover arranged on the holder component 1.

FIG. 6b shows a cross-section through the holder component 1 in the area of the switchable valve 86, cf. the sectional plane SE2. The compression die 12 has a foot 87 which is pressed by a spring 17 (in the present case a pressure spring) against a first sealing ring 15a, thereby blocking a gas flow from the pressure gas connection 13 from the space 89 around the spring 17.

By pressing the compression die 12, in the present case to the right-hand side cf. FIG. 6c, the spring 17 is compressed, thereby enabling a gas flow from the pressure gas connection 13 around the foot 87, past the seal 15a into a channel 88 in which the compression die 12 is guided. The female Luer connection (gas port) 11 terminates in this channel 88 such that a gas flow to the female Luer connection 11 is then enabled. An attached disposable syringe 4 that is inserted with its male Luer connection 41 into the matching female Luer connection 11 can be filled with inert gas in a corresponding fashion. The channel 88 is sealed on the left-hand side by a further seal 15b seated on the compression die 12, thereby preventing waste of inert gas as well as introduction of atmospheric oxygen.

As soon as the compression die 12 is no longer manually pressed, the compression die 12 is moved back to the left-hand side and the gas flow from the pressure gas connection 13 to the female Luer connection (gas port) 11 is interrupted again.

If required, the switchable valve 86 can be rinsed with inert gas prior to attachment of the disposable syringe 4, e.g. by pressing the compression die 12.

Since the female Luer connection 11 of the holder component 1 is located very close to the opening 10, in particular on the same side (upper side) of the holder component 1, the disposable syringe 4 can be very quickly changed between the female Luer connection (gas port) 11 and the female Luer connection 30 of the disposable cannula below the opening 10, which prevents or minimizes oxygen contamination.

Figure 7:
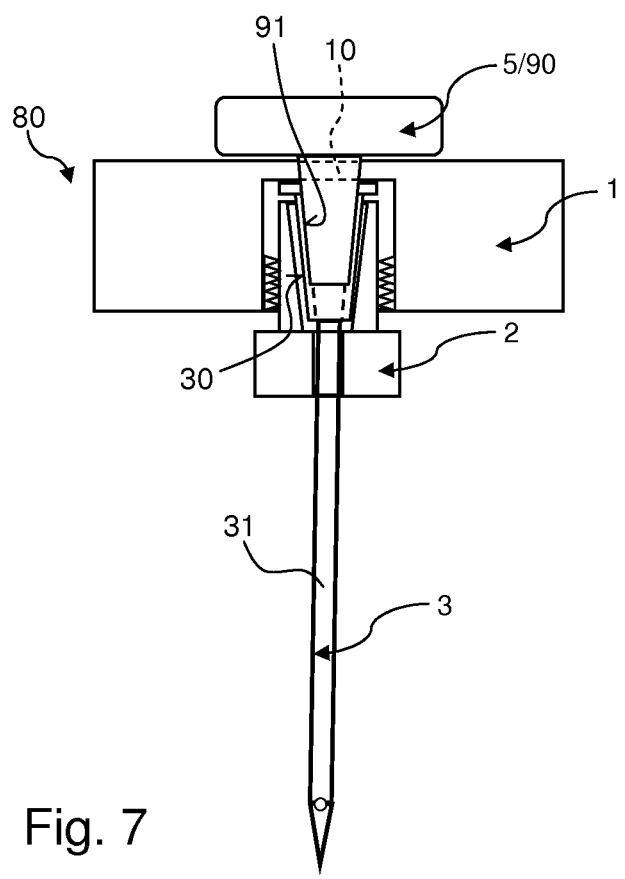
FIG. 7 shows a schematic cross-sectional view of the device of FIG. 3 with attached stopper.

FIG. 7 shows a cross-section of a device 80 similar to FIG. 3 with clamped disposable cannula 3 and with a cover component 5, in the present case designed as a stopper 90 with a male Luer connection 91. The stopper 90 is placed onto the opening 10 such that the male Luer connection 91 of the stopper 90 is seated in the female Luer connection 30 of the disposable cannula 3.

The disposable cannula 3 is driven with the device 80 with placed stopper 90 into the closure of the wine bottle such that in case the hollow needle 31 becomes detached from the female Luer connection 30, the hollow needle 31 does not injure the user. The hand of the user is typically positioned on the stopper 90. The stopper 90 blocks advance of the detached hollow needle 31 in an upward direction through the opening 10.

Figure 8:
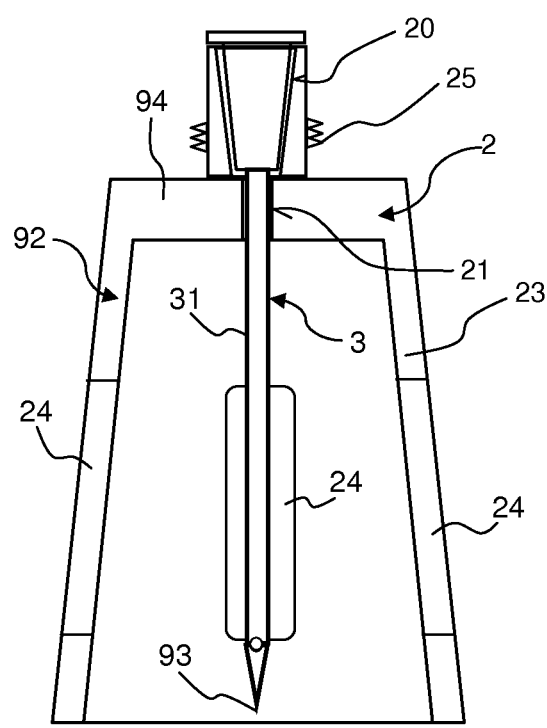
FIG. 8 shows a guide component for the invention with bell-like sleeve and with inserted disposable cannula.

FIG. 8 shows an embodiment of a guide component 2 in which a bell-shaped sleeve 92 is formed at the bottom of the guide component 2. In this case, the bell-shaped sleeve 92 has a ceiling section 94 and an approximately conical wall section 23. It is used for centering the guide component 2 or an inventive device on the bottle neck of a wine bottle. The bell-shaped sleeve 92 also prevents the user from being injured by the tip 93 of the hollow needle 31. The bell-shaped sleeve 92 projects past this tip 93 in an axial direction (in FIG. 8 from the top to the bottom). For this reason, the guide component 2 can also be easily disposed on a flat support without damaging or soiling the hollow needle 31.

In the illustrated embodiment, the bell-shaped sleeve 92 has a plurality of viewing windows 24 through which positioning of the tip 93 on the closure of the wine bottle can be viewed. The viewing windows are preferably formed by a transparent plastic material but may also be simply designed in the form of openings.

Figure 9A:
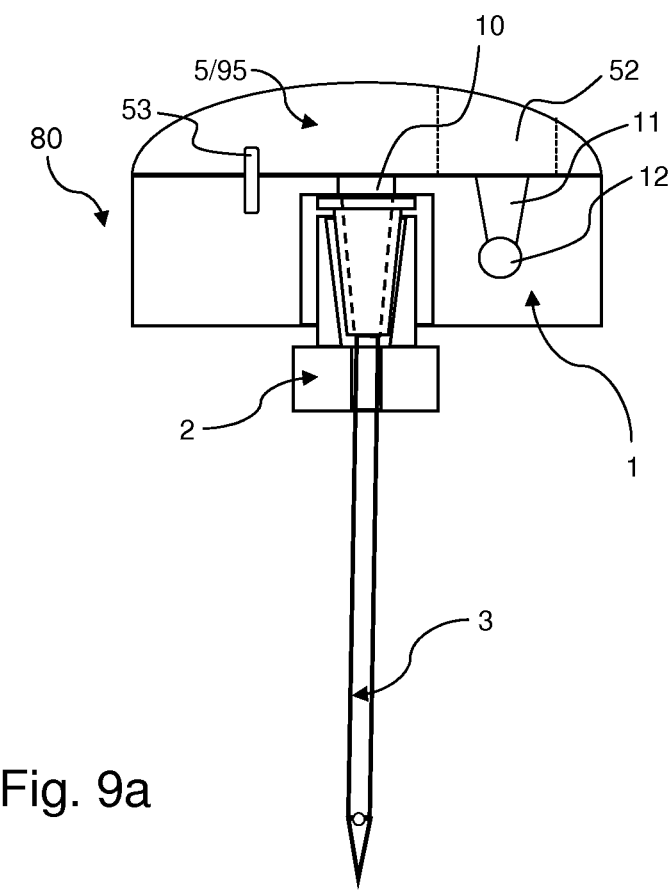
FIGS. 9a, 9b show a schematic cross-sectional view (FIG. 9a) and a schematic top view (FIG. 9b) of a device for performing the method in accordance with the invention with pivotable lid on the holder component, with closed puncture opening.
Figure 9B:
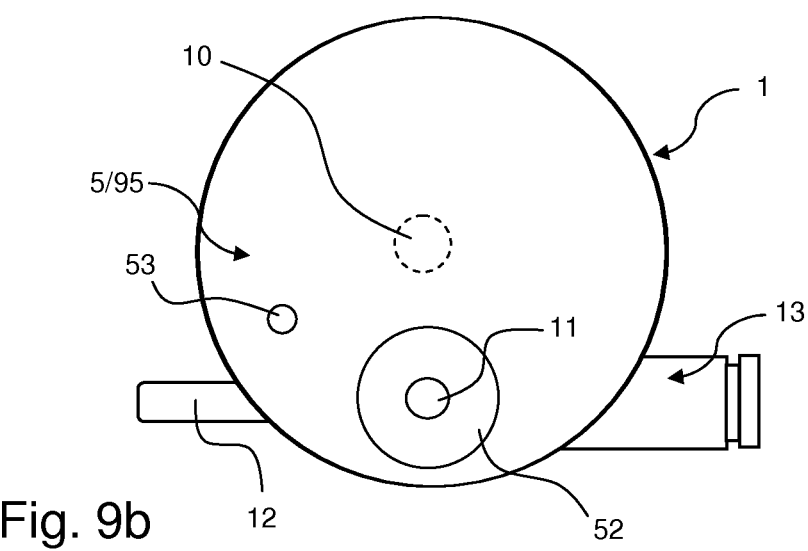

FIGS. 9a and 9b present an embodiment of an inventive device 80 in cross-section (FIG. 9a) and in top view (FIG. 9b), in which the holder component 1 is formed with a cover component 5 designed as a pivotable lid 95. The lid 95 can be rotated about a pin 53 that is eccentrically arranged. The lid 95 has a recess (access opening) 52 which can be pivoted over the female Luer connection (gas port) 11 of the holder component 1 or over the opening 10 of the holder component 1 in dependence on the pivot position of the lid 95.

In the pivot position illustrated in FIGS. 9a and 9b, the lid 95 is in a basic position in which the lid is positioned such that it substantially completely covers the holder component 1 and the recess 52 opens access to the female Luer connection 11. In this basic position, the device 80 can be easily gripped in order to push the disposable cannula 3 into the closure of the wine bottle. The lid having a rounded upper side is ergonomically formed and therefore comfortable to grip. The disposable syringe (not shown but cf. FIGS. 6a-6c) can also be filled with inert gas via the female Luer connection.

Figure 9C:
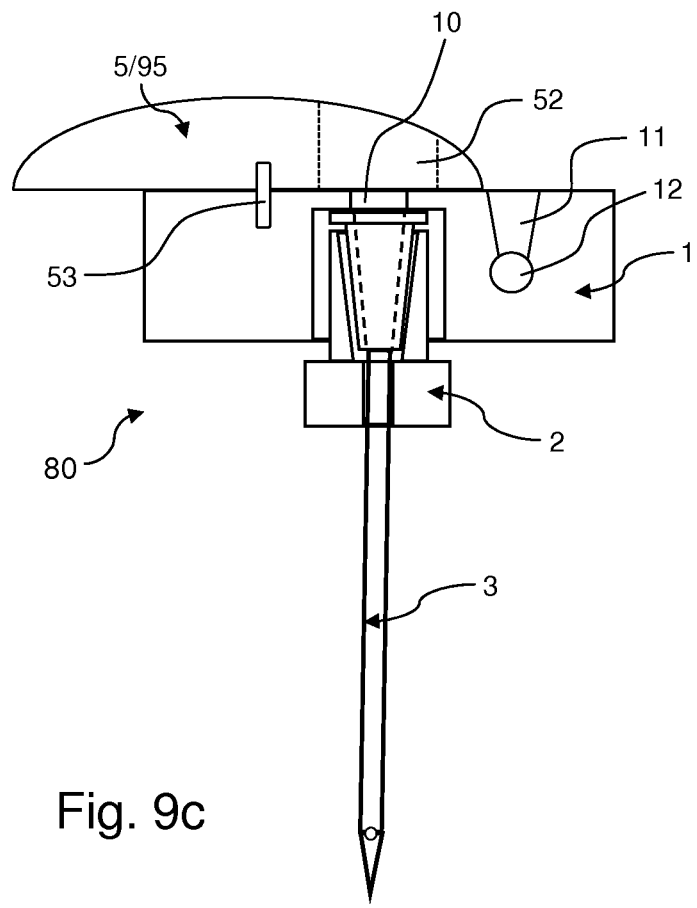
FIGS. 9c, 9d show a schematic cross-sectional view (FIG. 9c) and a schematic top view (FIG. 9d) of the device of FIGS. 9a, 9b with open puncture opening.
Figure 9D:
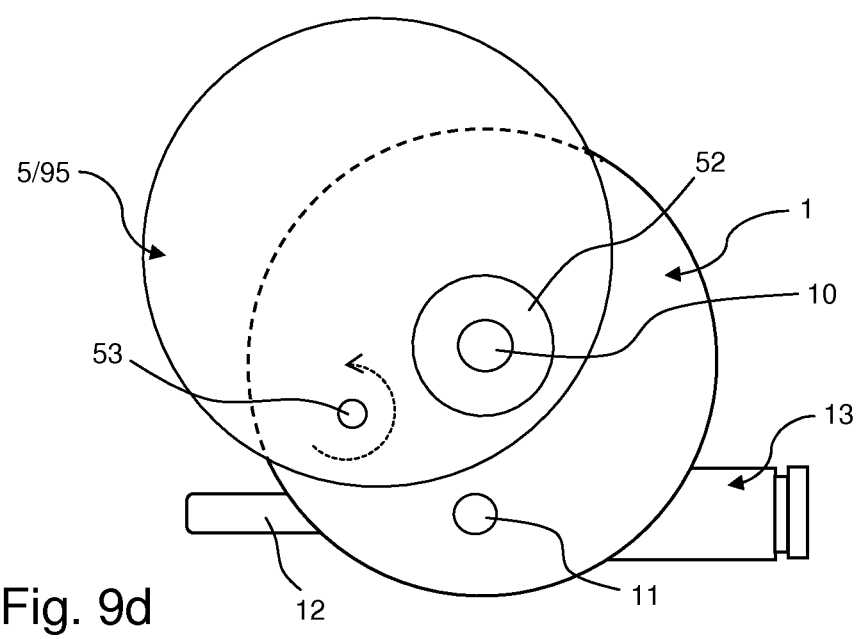

In the pivoted position of the lid 95, illustrated in cross-section in FIG. 9c and in top view in FIG. 9d, the lid partially projects (FIG. 9d left upper side) past the holder component 1. The recess 52 enables access to the opening 10 of the holder component 1 such that the disposable syringe (not shown, cf. FIG. 5) can be inserted with its male Luer connection (spout) into the female Luer connection 30 of a disposable cannula 3 that is being held. The wine bottle can then be filled with inert gas and the wine sample can be withdrawn.

Summarizing Overview for the Use of the Inventive Device During Withdrawal of the Sample Within the scope of the present invention, a holder (holder component) which has the size of approximately the palm of a hand is used as a power assistance for cannulas during puncture of the cork. The large surface of the holder facilitates power transmission during penetration of the cork.

The holder is coupled with a needle guide (guide component) for secure and stable fastening of a cannula. Coupling is realized via a quickly releasable coupling mechanism ("quick-connect device"), e.g. a thread or a bayonet closure for simple and quick change of the used cannulas. A suitable opening (through opening) in the holder allows easy and liquid-tight connection of a single-use syringe (disposable syringe) to a mounted single-use cannula (disposable cannula) with the assistance of the LUER function.

The holder preferably comprises an inert gas supply with a gas port for filling the single-use syringe with inert gas. The holder comprises a gas valve that is easy to operate for controlling filling of the single-use syringe with inert gas.

The single-use syringe should be filled with inert gas at a position close (e.g. less than 4 cm away) to the connection to the single-use cannula in order to ensure quick change of the position from the gas port to the cannula port after filling the single-use syringe with inert gas. This minimizes penetration (diffusion) of ambient air into the single-use syringe that is filled with inert gas.

The following process illustrates the typical withdrawal of a sample:
provision of the materials
  cannula (disposable cannula)
  syringe (disposable syringe)
  holder and needle guide (inventive device)
  gas source with inert gas (e.g. $N_2$ for example in a pressure gas container connected to the gas connection of the holder)
  corked wine bottle
fitting of the cannula in the holder
puncture of the cork (a cover component, e.g. a Luer stopper, should be mounted for reasons of safety)
fitting of the syringe in the gas port
filling the syringe body with inert gas by opening the gas valve
relocating the syringe onto the cannula
transferring the inert gas from the syringe into the sample bottle
withdrawal of the sample by filling the syringe
removal of the holder from the bottle/cork
removal of the syringe with sample and, if necessary, discharge of the sample into a sample container for further processing
after each withdrawal of a sample, the cannula and syringe are changed in order to prevent cross contaminations between different samples.

I claim:

1. A method for analyzing wine, the method comprising the steps of:
   a) puncturing a closure of a wine bottle containing wine using a disposable cannula having a lateral cannula opening and a female Luer connection and filling a disposable syringe having a male Luer connection with an inert gas or with nitrogen gas;
   b) disposing the disposable syringe on the disposable cannula and pressing the inert gas contained in the disposable syringe into the wine bottle;
   c) drawing up the disposable syringe while the cannula opening of the disposable cannula is immersed in wine within the wine bottle such that the disposable syringe is at least partially filled with a sample of the wine;
   d) removing the disposable cannula from the closure of the wine bottle;
   e) transferring at least part of the wine sample into an analytical spectrometer; and
   f) carrying out spectrometric analysis of at least that part of the wine sample transferred into the analytic spectrometer in step e).

2. The method of claim 1, wherein a volume of inert gas filled into the disposable syringe in step a) is larger than or equal to a volume of the wine sample filled into the disposable syringe in step c).

3. The method of claim 1, wherein the disposable cannula is rinsed with inert gas or with nitrogen gas prior to puncture of the closure.

4. The method of claim 1, wherein a puncture opening of the closure is sealed in an air-tight fashion after removing the disposable cannula in step d).

5. The method of claim 4, wherein the puncture opening is sealed by a wax drop or a plastic cap.

6. The method of claim 1, wherein the disposable syringe is a disposable syringe with a return valve or a monovette.

7. The method of claim 1, wherein the spectrometric analysis is an NMR analysis.

8. A device for carrying out steps a) through d) of claim 1, the device comprising:

a guide component having a first coupling means, the guide component also having a guide channel for accepting the disposable cannula and a receptacle for accepting the female Luer connection of the disposable cannula, wherein the female Luer connection has a collar, the guide component further comprising a bell-like sleeve for receiving a bottle neck of the wine bottle; and a holder component, the holder component defining a stop for the collar of the female Luer connection of the disposable cannula, the holder component furthermore having a puncture opening providing access for the male Luer connection of the disposable syringe to the female Luer connection of the disposable cannula when the disposable cannula abuts the stop, wherein the holder component further comprises a second coupling means that cooperates with the first coupling means for reversibly fastening the guide component to the holder component.

9. The device of claim 8, wherein the first coupling means has an outer thread and the second coupling means has an inner thread.

10. The device of claim 8, wherein the receptacle of the guide component forms an anti-twist protection for the disposable cannula.

11. The device of claim 10, wherein the receptacle of the guide component has two longitudinal slots or longitudinal grooves for engagement of two vanes formed on the female Luer connection of the disposable cannula.

12. The device of claim 8, wherein the bell-like sleeve projects past a tip of the disposable cannula when the disposable cannula is accommodated in the guide component.

13. The device of claim 8, wherein the bell-like sleeve has one or more viewing windows.

14. The device of claim 8, wherein the device further comprises a cover component for covering the puncture opening of the holder component on a side facing away from the stop.

15. The device of claim 14, wherein the cover component is designed as a stopper or as a stopper having a male Luer connection.

16. The device of claim 14, wherein the cover component is a lid that is rotatably or displaceably mounted on the holder component and has a recess that can be pivoted or displaced over the puncture opening.

17. The device of claim 8, wherein the holder component further comprises a pressure gas connection for the inert gas, a female Luer connection and a manually switchable valve, wherein the female Luer connection of the holder component is connected to the pressure gas connection via the switchable valve.

18. The device of claim 17, wherein the switchable valve is pretensioned into a closed position by a spring.

19. The device of claim 17, wherein the female Luer connection of the holder component is arranged on a same side of the holder component as a side of the puncture opening facing away from the stop.

20. A method for analyzing wine using a device, the device comprising:

a guide component having a first coupling means, the guide component also having a guide channel for accepting a disposable cannula and a receptacle for accepting a female Luer connection of the disposable cannula, wherein the female Luer connection has a collar; and a holder component, the holder component defining a stop for the collar of the female Luer connection of the disposable cannula, the holder component furthermore having a puncture opening providing access for a male Luer connection of a disposable syringe to the female Luer connection of the disposable cannula when the disposable cannula abuts the stop, wherein the holder component further comprises a second coupling means that cooperates with the first coupling means for reversibly fastening the guide component to the holder component;

the method comprising the steps of:

a) puncturing a closure of a wine bottle containing wine using the disposable cannula, the disposable cannula having a lateral cannula opening, and filling the disposable syringe with an inert gas or with nitrogen gas;

b) disposing the disposable syringe on the disposable cannula and pressing the inert gas contained in the disposable syringe into the wine bottle;

c) drawing up the disposable syringe while the cannula opening of the disposable cannula is immersed in wine within the wine bottle such that the disposable syringe is at least partially filled with a sample of the wine;

d) removing the disposable cannula from the closure of the wine bottle;

e) transferring at least part of the wine sample into an analytical spectrometer; and f) carrying out spectrometric analysis of at least that part of the wine sample transferred into the analytic spectrometer in step e), wherein, for steps a), b), c) and d), the disposable cannula is held between the guide component and the holder component and abuts the stop and the disposable syringe is inserted through the puncture opening into the disposable cannula, at least during steps b) and c).

* * * * *